United States Patent [19]
della Valle et al.

[11] Patent Number: 4,595,680
[45] Date of Patent: Jun. 17, 1986

[54] PHARMACEUTICAL COMPOSITIONS AND METHOD FOR PREPARING PHOSPHATIDYLSERINE COMPOSITIONS USEFUL IN TREATING CENTRAL NERVOUS SYSTEM DISORDERS WITHOUT EFFECTS ON BLOOD COAGULATION

[75] Inventors: Francesco della Valle, Padua; Aurelio Romeo, Rome, both of Italy

[73] Assignee: FIDIA, S.p.A., Abano Terme, Italy

[21] Appl. No.: 599,341

[22] Filed: Apr. 12, 1984

[30] Foreign Application Priority Data

Nov. 17, 1983 [IT] Italy .................... 49355 A/83

[51] Int. Cl.$^4$ ............................................. A61K 31/685
[52] U.S. Cl. ............................................................. 514/77
[58] Field of Search ............................ 424/199; 514/77

[56] References Cited

U.S. PATENT DOCUMENTS 3,156,616 11/1964 Mustard ................................. 514/79
3,436,413 4/1969 Okany ................................... 514/77
4,078,052 3/1978 Papahadjopoulos ................. 424/36

FOREIGN PATENT DOCUMENTS 5060 12/1965 France .................................. 514/77

OTHER PUBLICATIONS

Zwall, R., Biochem. Biophys. Acta., 515 (1978) 163–205.
Bruni et al., Nature, 260 (1976) 331–333.
Toffano et al., Internat. Multidisc. Sem.: "Cerebral Path. in Old Age", 2nd Ed., 1983.

Primary Examiner—Stanley J. Friedman
Assistant Examiner—John W. Rollins
Attorney, Agent, or Firm—Birch, Stewart, Kolasch & Birch

[57] ABSTRACT

A phospholipid composition comprised of a mixture of phosphatidylserine and phosphatidylethanolamine in a specified ratio having activity against disorders of the central nervous system but without secondary haematic coagulation effects. Particularly useful compositions comprise from 60 to 75% by weight of phosphatidylserine and from 40 to 25% by weight of phosphatidylethanolamine.

21 Claims, No Drawings

PHARMACEUTICAL COMPOSITIONS AND METHOD FOR PREPARING PHOSPHATIDYLSERINE COMPOSITIONS USEFUL IN TREATING CENTRAL NERVOUS SYSTEM DISORDERS WITHOUT EFFECTS ON BLOOD COAGULATION

BACKGROUND AND FIELD OF THE INVENTION

The present invention relates to a phospholipid composition which is administered by various routes for treating disorders of the central nervous system, particularly those connected with aging of the brain.

Phospholipids are a large class of lipids characterized by a glycerol portion which binds phosphate and fatty acids. The general formula in phospholipids is as follows:

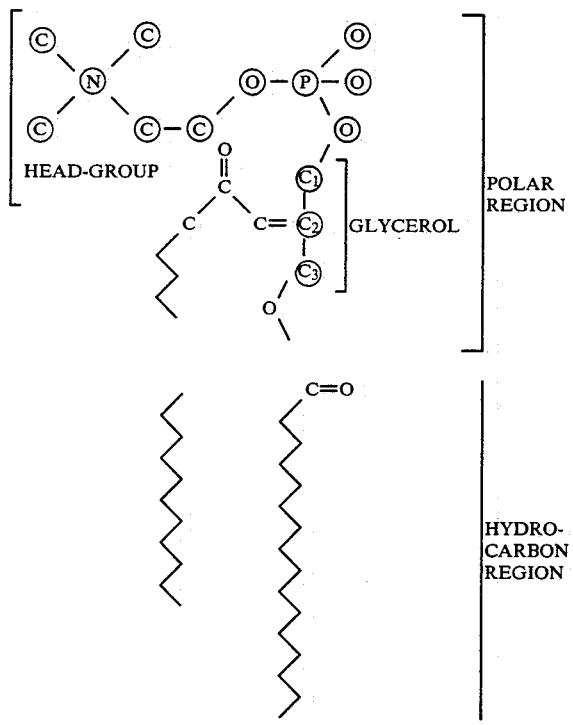

or,

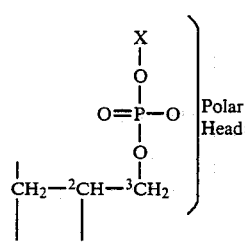

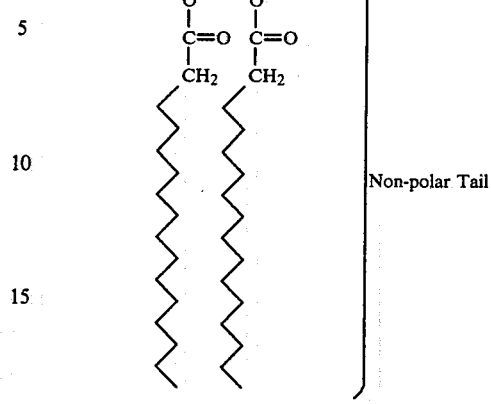

wherein X is a particular polar head group characterizing the different phospholipid classes. (See Lehninger, Biochemistry, 2 Ed., p. 288).

It is understood that the role of phospholipids in haematic coagulation is crucial but not yet altogether clear. Indeed, on a molecular level, the interaction of phospholipids during this process with coagulation factors is still to be explained.

By outlining the intrinsic and extrinsic coagulation pathways it is possible to observe that phospholipids play a key role in the coagulation cascade. In fact, phospholipids constitute 30-50% of crude thromboplastin preparations, and their composition varies according to the origin of the preparation. The major part, however, is constituted by phosphatidylcholine (PC) and phosphatidylethanolamine (PE), while negatively charged phospholipids such as phosphatidylserine (PS) and phosphatidylinositol (PI) account for a small part (Liu D. T. H. et al. Thromb. Res. 7 (1975) 213-221). The polar group of the phospholipid plays an essential role in the formation of the complexes in the coagulation pathway (Otnaes A. B. et al Eur. J. Biochem. 27, (1972), 238-243; Nemerson Y. Adv. Exp. Med. Biol. 63, (1975) 245-253).

Regarding the specificity of the polar head, it has been observed that by recombining the tissue factor apoprotein with PE, thromboplastic activity is completely restored (Nemerson Y., supra; Liu D. T. H. et al., supra). PC proves to be less active, while other phospholipid fractions and PE have no activity at all, despite the fact that they bind to the apoprotein fraction. According to Wijngaards et al. (Biochem. Biophys. Acta 488, (1977), 161-171) lipid mixtures with moderate negative charges are necessary for a complete restoration of thromboplastin activity.

Also, the role of externally added phospholipids is not altogether clear. Indeed, there is evidence in the literature that phospholipid preparations from cerebral tissue, prepared by extraction in chloroform and dried in acetone, act in vitro as strong coagulants (Bell, W. M. et al. Nature 174 (1954), 880-881), while phospholipid mixtures extracted from cerebral tissue with chloroform:methanol followed by removal of the nonlipidic parts with saline have proved to be virtually inactive (Folch, H. et al. J. Biol. Chem. 226, (1957), 497-509). It should be noted that in the first case cerebral tissue proteins were present, while in the second case they had been eliminated by the partitioning process.

The composition and purity of the phospholipids used is still the fundamental factor in understanding their exact role, considering also the fact that different activities have been reported for the individual particular classes of phospholipid. It is, however, the correlation between negative charge and coagulant activity which makes phosphatidylserine particularly interesting for these phenomena. The activity of PS is debated with some authors in fact claiming that PS has a catalytic action (Marcus A. J. Adv. Lip. Res. 4 (1966) 1–37), while others report an inhibitory activity of PS (Turner D. L. et al. J. Lip. Res. 5 (1964) 616–623) due to the formation of inactive complexes. Mustard et al. also report (Nature, 196 (1962) 1963–1065) an anticoagulant activity of PS when injected in vivo in dogs in a range of dosages between 30 and 50 mg/kg. In addition, it has been reported that PE has a marked coagulant activity (Rouser et al. Biochem. Biophys. Acta 28 (1958) 71–80; Turner D. L. et al. J. Lip. Res. 4 (1963) 52–56). The activity of a mixture of at least two classes of phospholipid is, however, probably more interesting than that of the single classes.

Some preparations with considerable activity are binary compositions with PE/PS (65/35 w/w), PC/PS (57/43 w/w), PC/PG (48/52 w/w and PG/stearoylamine (85/15 w/w) (Zwaal R. F. A. Biochem. Biophys. Acta 515, (1978), 163–205).

The binary mixture of PS/PC in the presence of calcium seems important in the formation of the coagulation pathway complexes (Subbaiah E. V. et al. Biochem. Biophys. Acta 444, (1976), 131–146). When PS constitutes 25% of the mixture with other phospholipids it proves to be critical in determining, in this range, the maximum biological activity in the conversion from prothrombin and thrombin (M. F. Lecompte et al. J. Electro. Anal. Chem. 104 (1979) 537–541).

It should be observed that this phospholipidic fraction, namely phosphatidylserine, is also interesting for other biological and pharmacological activities.

In fact, a wide range of implications of phosphatidylserine in various biological processes has been reported in the literature. In summary, the biological implications of PS in physiological phenomena are the following:

(a) PS restores ASPase activity associated with isolated neuronal membranes (Wheeler and Whittam (1970), Nature 225, 449–450; Palatini et al (1977) Biochem. Biophys. Acta 466, 1–9).

(b) PS stimulates activity of isolated tyrosine hydroxylase enzyme (Lloyd and Kaufmann (1974) Biochem. Biophys. Res. Comm. 59, 1262–1269; Raese et al. (1976) Biochem. Pharmacol. 25, 2245–2250).

(c) PS liposomes induce cell fusion (Papahadjopoulos et al. (1973) Biochem. Biophys. Acta 323, 23–42).

In addition to the biochemical effects observed, several lines of investigation have shown that cerebral metabolism is influenced by the in vivo administration of PS; the activity of dopaminergic and cholinergic systems is greatly affected, probably by an intervention on presynaptic mechanisms regulating neurotransmitter release. This activity is reflected in measurable effects on several neuroendocrine, electrophysiological and behavioral correlates.

In particular, Bruni et al (Nature 260 (1976) (5549), 331–333) reported a significant biological effect of PS in vivo on cerebral carbohydrate metabolism by measuring an increase of the cerebral glucose haematic ratio. Other phospholipids proved unable to induce this effect.

This cerebral activation after injection in vivo of PS was confirmed by Toffano et al (Life Sciences 23, (1978) 1093–1102), who showed that in cerebral neurotransmitter systems the intravenous (i.v.) injection of PS increased the turnover rate of norepinephrine in the hypothalamus. This hypothalamic effect was accompanied by an increase in the affinity of tyrosine hydroxylase for its synthetic pteridine cofactor (Toffano, Battistin, "*Neurochemistry and Clinical Neurology*", (1980) 205–214) and by an increase of cAMP.

These effects are correlated with an increase of acetylcholine (ACh) output from the cerebral cortex in urethane-anaesthetised rats (Casamenti et al. J. Neurochem. (32 (1979) 529–533). When ACh levels in rat cerebral cortex were measured, it was found that PS (30 mg/kg i/p. for 10 days) potentiated the effect of the antimuscarinic drug scopolamine (Mantovani et al., *Phospholipids in the Nervous System*-Vol. 1, (1981) 165–172).

The effect of PS on cerebral neurotransmitter systems is supported by neuroendocrine, electrophysiological and behaviorial correlates. Canonico et al. (Neuroendocrinology 33, (1981) 358–362) described the effects of PS on prolactin secretion in rats. The drug, in acute or repeated administration, reduced plasma prolactin levels during different phases of the circadian rhythm and inhibited the plasma prolactin surge typical of the proestrus afternoon in female rats.

On the other hand, a series of experiments (Mantovani et al., supra; Toffano et al., *New Trends in Nutrition Lipid Research, and Cardiovascular Diseases*, (1981) 91–99) showed that the typical disruption of EEG pattern induced by the anticholinergic drug scopolamine was efficiently antagonized by previous or simultaneous administration of PS.

Subsequently, Aporti et al. (Res. Comm. Psychol. Psych. Behav. 7 (1982) (1), 131–143) extended the EEG investigations by using computerized analysis of EEG recorded by means of implanted cortical and subcortical electrodes in freely moving rats. Acute administration of PS produced, at a cortical level, a reversal of the pre-drug ratios of the amplitudes in the right and left hemispheres. The effect became most pronounced at the end of 10 days of chronic administration.

This effect is correlated to a typical instinctive explorotory behavior, defined as alternation, and exhibited by rats placed in a T-maze set-up. Also this typical behavior is disrupted by the anticholinergic drug scopolamine. Pepeu et al. (Aging Br. Dementia 13, (1980) 271–274) reported that intraperental (i.p.) administration of PS completely antagonized the disrupting effect of scopolamine on spontaneous alternation in a T-maze.

More recently, Toffano et al. (International Multidisciplinar Seminar: "Cerebral Pathology in Old Age", Second Edition (In press 1983)) reviewed pharmacological data obtained in aged animals, in order to evaluate the protective effects of PS on parameters which undergo changes with age. Injection of PS favorably influenced several biochemical membrane parameters, including stimulation of ($Na^+K^+$)-ATPase, and antagonism of age-related alternations of the cholesterol to phospholipid molar ratio. Concomitantly, PS prevented the age-dependent decrease of dopamine and its catabolites in rat striatum and limbic areas.

In addition, a series of studies confirmed a favorable effect of PS on learning and memory processes in aged rats. Positive effects of PS on cognitive functions in aged rats were reported by Drago and Scapagnini, *Neurobiology of Aging* 2, (1981) 209-213.

In summary, pharmacological data reported in the literature make it evident that administration to man of pharmaceutical compositions containing PS of cerebral origin and with a high degree of purity may represent a valid therapeutic means for treating aging of the brain where a diminishing of dopaminergic control is well known. On the other hand, data reporting the effects of PS on blood coagulation suggest a grave risk of haemorrhage upon administration of PS. This is a particular disadvantageous risk in elderly patients who often already suffer from vascular complications.

OBJECTS AND SUMMARY OF THE INVENTION

It is therefore one object of the present invention to provide a pharmaceutical composition of phosphatidylserine useful for the treatment of conditions resulting from aging of the brain.

It is another object of the present invention to provide a phosphatidylserine pharmaceutical composition which does not have undesirable secondary effects on blood coagulation.

It is a further object of the invention to provide a pharmaceutical composition of phosphatidylserine and a method for treating disorders of the central nervous system which are caused by a decreased dopaminergic control.

It is still a further object of the present invention to provide a composition of phospholipids comprising PS which is active against central nervous system disorders but which does not have undesirable side effects, particularly vascular complications.

These and other objects of the present invention are accomplished by providing a phospholipid composition comprised of a mixture of phosphatidylserine and phosphatidylethanolamine in a specified ratio having activity against disorders of the central nervous system but without secondary haematic coagulation effects.

DESCRIPTION OF THE INVENTION

The present invention basically resides in identifying new phospholipid compositions by means of which highly pure phosphatidylserine can be administered to humans by various routes with pharmacological activity on the nervous system, but without undesirably altering coagulation of the blood. The specific pharmacological profile of the compositions consists of dopaminergic control modulation. The compositions are, therefore, particularly useful for treatment of pathologies which are characterized by decreased dopaminergic control; namely involution of the senile psychomotor syndromes, vascular cerebropathy, chronic and prevalent psychic component in old age, senile dementia and pre-senile syndromes subjective to post-trauma, post-anoxic cerebropathy, and extrapyramidal syndromes.

In treating these various pathologies, it is necessary to eliminate whatever secondary haematic coagulation effects may arise upon administration of the compositions. In fact, it is well known that vascular complications often occur in old age, so that, haematic coagulation effects must be considered in the treatment of these pathologies. The phospholipid compositions of the invention are comprised of phosphatidylserine which is extracted from the brain tissue of animals. These particular compositions do not have any undesirable effects on blood coagulation.

Detailed studies have been conducted on the effect on coagulation of a mixture of phospholipids extracted and purified from bovine brain cortex. These studies have also determined the effects of purified phosphatidylserine and binary mixtures of phosphatidylserine with other single classes of phospholipids (PE, PC and sphingomyelin). This research was conducted with an aim toward obtaining a pharmacologically active phosphatidylserine preparation which has no undesirable side effects on haematic coagulation. Specific evaluation was made of the central nervous system activity effects of in vivo administration of the phospholipid compositions together with any side effects on haematic coagulation which may occur.

Methods:

The activity of the various products has been evaluated in vivo by intravenously injecting various phospholipid preparations in New Zealand rabbits weighing 1.5-2 kg, at dosages ranging from 0.5 mg/kg to 50 mg/kg. The phospholipids were placed in phosphate buffer (pH 7.4) and sonicated until the suspension became clear (all possible traces of titanium from the sonicator were eliminated by means of centrifugation). After treatment, blood was drawn from the animals and tested for coagulation. Determinations were carried out using hemocoagulation kits supplied by Biochemia (Boheringer, Mannheim) with a Digiclot Elvi 818 apparatus, on plasma obtained by centrifugation at a speed of 4,200 r.p.m. for 10 minutes of blood in 3.8% sodium citrate at a ratio of 1:9. The parameter considered was prothrombin time according to Quick.

The pharmacological activity of the individual product compositions tested was evaluated by measuring mouse cerebral glucose in the same dosage range, considering this parameter as an indication of cerebral activation. For this experiment Swiss mice weight between 20-25 gr were treated and sacrificed 30 minutes after injection. Glucose levels were measured as described by Bruni et al. in Nature 260, (1976) 331-333.

The individual compositions tested were as follows:
(1) phosphatidylserine (PS) from the bovine brain cortex with a titer of over 90%;
(2) phosphatidylserine+phosphatidylethanolamine (BC-PS) with 75% PS and 25% PE w/w;
(3) phosphatidylserine+phosphatidylethanolamine (BC-PS$_1$) with a 65% PS and 35% PE w/w;
(4) phosphatidylserine+phosphatidylethanolamine (BC-PS$_2$) with a 60% PS and 40% PE w/w;
(5) phosphatidylserine+phosphatidylethanolamine (BC-PS$_3$) with a 50% PS and 50% PE w/w;
(6) phosphatidylserine+phosphatidylethanolamine (BC-PS$_4$) with a 40% PS and 60% PE w/w;
(7) phosphatidylserine+phosphatidylethanolamine BC-PS$_5$) with a 25% PS and 75% PE w/w;
(8) phosphatidylserine+phosphatidylethanolamine BC-PS$_6$) with a 85% PS and 15% PE w/w;
(9) phosphatidylserine+phosphatidylcholine BC-PS$_7$) with a 75% PS and 25% PC w/w;
(10) phosphatidylserine+spingomyelin BC-PS$_8$) with a 75% PS and 25% SF w/w.

Results:

The results from the above-described tests are summarized below in Tables 1 and 2.

TABLE 1

Activity of various phospholipid compositions on haematic coagulation and on cerebral glucose recorded 30 minutes after in vivo treatment at a dosage of 20 mg/kg i.v. of different mixtures.

| Percentage of Phospholipids in the composition mixture | Dosage (mg/kg)[a] Total Dose of Composition Mixture | Compound Dose of PS | Prothrombin time according to Quick (sec.) | Cerebral glucose (umole/g) |
|---|---|---|---|---|
| Controls | — | — | 7.43 ± 0.07 | 1.3 |
| PS | 20 | 20 | 12.34 ± 0.8 | 4.1 |
| BC-PS (PS 75 PE 25) | 20 | 15 | 7.36 ± 0.14 | 3.7 |
| BC-PS$_1$ (PS 65 PE 35) | 20 | 13 | 7.5 ± 0.3 | 3.5 |
| BC-PS$_2$ (PS 60 PE 40) | 20 | 12 | 7.8 ± 0.5 | 3.2 |
| BC-PS$_3$ (PS 50 PE 50) | 20 | 10 | 8.5 ± 0.2 | 3.0 |
| BC-PS$_4$ (PS 40 PE 60) | 20 | 8 | 6.7 ± 0.9 | 2.5 |
| BC-PS$_5$ (PS 25 PE 75) | 20 | 5 | 6.5 ± 0.2 | 1.9 |
| BC-PS$_6$ (PS 85 PE 15) | 20 | 17 | 11.3 ± 1.2 | 2.9 |
| BC-PS$_7$ (PS 75 PC 25) | 20 | 15 | 9.3 ± 0.7 | 3.0 |
| BC-PS$_8$ (PS 75 SF 25) | 20 | 15 | 14.7 ± 0.9 | 3.1 |

[a]The dosage of the composition mixture was maintained at a constant rate of 20 mg/kg. Therefore the dosage of PS varied according to the corresponding percentage of PS in each mixture.

TABLE 2

Activity of the various phospholipid compositions on hematic coagulation and on cerebral glucose recorded 30 minutes after in vivo treatment of a dosage of 20 mg/kg i.v. of PS.

| | Dosage (mg/kg)[a] Compound Dose of PS | Total Dose of Composition Mixture | Prothrombin time (sec.) | Cerebral glucose (umole/kg) |
|---|---|---|---|---|
| Control | — | — | 7.43 ± 0.07 | 1.3 |
| PS | 20 | 20 | 12.34 ± 0.8 | 4.1 |
| BC-PS | 20 | 27 | 7.5 ± 0.20 | 4.3 |
| BC-PS$_1$ | 20 | 30.7 | 8.0 ± 0.2 | 4.1 |
| BC-PS$_2$ | 20 | 33.3 | 8.2 ± 0.7 | 3.8 |
| BC-PS$_3$ | 20 | 40 | 9.5 ± 0.3 | 3.8 |
| BC-PS$_4$ | 20 | 50 | 4.2 ± 9.3 | 4.0 |
| BC-PS$_5$ | 20 | 80 | 3.5 ± 0.4 | 3.3 |
| BC-PS$_6$ | 20 | 23.5 | 13.3 ± 0.2 | 3.6 |
| BC-PS$_7$ | 20 | 27 | 11.5 ± 0.3 | 3.8 |
| BC-PS$_8$ | 20 | 27 | 12.3 ± 0.5 | 3.9 |

[a]The dosage of PS was maintained at a constant rate of 20 mg/kg. In order to achieve this constant dosage rate of PS, the dosage rate of the total composition mixture varied according to the corresponding percentage of PS in each mixture.

From the results measuring the coagulation parameters, it is possible to observe a clear anticoagulant activity after administration of pure phosphatidylserine in vivo, which confirms previous observations of Mustard et al. (Nature 196, pages 1063-1065 (1965)).

In the case of the binary mixtures of PS plus other phospholipids, the anticoagulant activity varies with different rates according to the particular type of phospholipid associated with PS. But in the case of BC-PS, the measured prothrombin time is essentially the same as that for the controls, indicating that this composition has no undesirable effect on blood coagulation.

Further analysis of the results reported in Tables 1 and 2 shows that phosphatidylserine is the most active fraction for increasing brain glucose levels. This effect can also be observed in the case of the binary mixtures of PS with other phospholipids, in a manner similar to that for pure PS. By considering the data reported in Table 2 with constant doses of 20 mg/kg i.v. of pure PS, it can be seen that cerebral activity is enhanced for all of the binary mixtures of phospholipids, as compared to the controls. However, the activity on blood coagulation is extremely varied depending upon the particular binary composition with some compositions shortening and others lengthening the measured times as compared to controls.

It is, therefore, of particular importance to note that the use of a binary mixture of PS and PE (particularly 75% PS plus 25% PE) exhibits no undesirable activity on coagulation, while it does have good activity on the central nervous system (CNS). That is, the PS composition comprised of a mixture of phospholipids exhibits good CNS activity as measured from the cerebral glucose level, but this composition also has undesirable hematic coagulation side effects as shown by the extended prothrombin time. On the other hand, the BC-PS$_4$ and BC-PS$_5$ compositions administered at constant dosage levels of the binary mixture exhibited decreased prothrombin times in a more acceptable range as reported in Table 1. However, these compositions (particularly BC-PS$_5$) did not exhibit sufficiently desirable CNS activity as evidenced by the low cerebral glucose levels. Moreover, in administering constant dosages of PS in a binary mixture, compositions of BC-PS$_4$ and BC-PS$_5$ also exhibited marked decreased prothrombin times such that the low prothrombin times for the BC-PS$_5$ composition actually represent an undesirable side effect in causing coagulation of the blood at a rate that is too fast. This effect would lead to a risk of thrombosis in patients treated with these mixtures.

The fractions of PS with PC, and PS with SF were also found to be undesirable in that they exhibited extended prothrombin times.

It has, however, been determined by the present inventors that the BC-PS, BC-PS$_1$ and BC-PS$_2$ compositions do represent useful pharmaceutical compositions. All three of these compositions exhibit an acceptable prothrombin time substantially reduced from the prothrombin time of PS and comparable to that of the controls, while at the same time exhibiting good CNS activity as shown by the cerebral glucose levels.

It has, therefore, been determined in accordance with the present invention that a preferred phospholipid composition having good CNS activity and without undesirable hematic coagulation effects is obtained by preparing a mixture of from 60 to 75% PS with from 40 to 25% PE. More preferably, the composition should contain about 75% PS and 25% PE. The following examples describe specific pharmaceutical compositions prepared according to the present invention useful for treating various disorders of the central nervous system by dopaminergic control modulation.

EXAMPLE 1

Preparation of the phospholipid composition BC-PS 1000 g of phosphatidylserine (PS) extracted from bovine nervous tissue with a titer of more than 95% are dissolved in 5 liters of a mixture of methanol:chloroform (2:1). 333 g of phosphatidylethanolamine (PE) with a titer of more than 80% are added to the solution.

The solution is kept in agitation for 30 minutes, filtered through a sterilizing membrane filter and precipitated in 5 volumes of acetone under suitable agitation.

The precipitate is separated and dried in vacuum at low temperature.

About 1250 g of a BC-PS composition are obtained in this way.

EXAMPLE 2

Preparation of the phospholipid composition $BC\text{-}PS_1$

In the same manner as in Example 1, 1000 g of PS with a titer of more than 95% are dissolved in 5 liters of a mixture of methanol:chloroform (2:1) and 538 g of PE with a titer of more than 80% are added to the solution.

After agitation, filtering, precipitation, and drying, about 1442 g of a $BC\text{-}PS_1$ composition are obtained.

EXAMPLE 3

Preparation of the phospholipid composition $BC\text{-}PS_2$

In the same manner as in Example 1, 1000 g of PS with a titer of more than 95% are dissolved in 5 liters of a mixture of methanol:chloroform (2:1) and 666 g of PE with a titer of more than 80% are added to the solution.

After agitation, filtering, precipitation, and drying, about 1562 g of a $BC\text{-}PS_2$ composition are obtained.

EXAMPLE 4

Examples of injectable pharmaceutical compositions (a) One 2 ml vial contains:
Liposomes of phospholipid composition BC-PS: 66.5 mg
monobasic sodium phosphate: 2.4 mg
dibasic sodium phosphate: 2.26 mg
pyrogen-free twice-distilled water: q.s. 2 ml
(b) One 5 ml vial contains:
Liposomes of phospholipids composition BC-PS: 332.5 mg
monobasic sodium phosphate: 5.35 mg
dibasic sodium phosphate: 6.65 mg
pyrogen-free twice-distilled water: q.s. 5 ml
(c) One 3 ml vial contains:
Liposomes of phospholipid composition BC-PS: 199.5 mg
monobasic sodium phosphate: 3.21 mg
dibasic sodium phosphate: 3.39 mg
mannitol: 30 mg The products described above in Example 4 can be utilized in emergency therapy against pathologies of the central nervous system. More specifically, these formulations can be used acutely in anoxic cerebropathy and extrapyramidal traumatic syndromes, pre-senile and senile dementia, as well as metabolic encephalopathy.

EXAMPLE 5

Examples of oral pharmaceutical compositions (a) Each gelatinous capsule contains:
phospholipid composition BC-PS: 133 mg
vegetable oil: 270 mg
beeswax: 1 mg
(b) Each gelatinous capsule contains:
phospholipid composition BC-PS: 332.5 mg
vegetable oil: mg
beeswax: mg
(c) Each pill contains:
phospholipid composition BC-PS: 66.5 mg
mannitol: 100 mg
microcrystalline cellulose: 25 mg
starch: 5 mg
saccharose: 30 mg
lacquer: 5 mg
(d) Each operculum contains:
phospholipid composition BC-PS: 199.5 mg
mannitol 100 mg
lactose 100 mg The products described above in Example 5 can be used in chronic therapies. Specifically these formulations can be used to treat involution of senile psychomotor syndromes, chronic vascular cerebropathy, metabolic encephalopathy in old age, senile dementia and pre-senile syndromes subjective to post-trauma, post-anoxic cerebropathy and extrapyramidal syndromes.

Although the above pharmaceutical compositions have been described in particular physical forms with particular carriers, it will be recognized that the pharmaceutical compositions of the invention can be formulated in other standard physical forms combined with other known pharmaceutically acceptable carriers, excipients and diluents.

From the above, it can be seen that the present invention provides a pharmaceutical composition useful for treating disorders of the central nervous system which are specifically related to aging of the brain. Compositions of the invention have good central nervous system activity while, at the same time, they do not exhibit undesirable side effects with respect to haematic coagulation. This discovery is particularly important in providing a means for treating central nervous system disorders with phospholipid compositions, since compositions containing only phosphatidylserine have such an undesirable effect on blood coagulation as to be nonusable as a pharmaceutical composition. The present inventors, however, have overcome this problem by discovering that a particular binary composition of phosphatidylserine with phosphatidyletholamine can provide a useful active pharmaceutical composition without the undesirable side effects encountered with administration of phosphatidylserine alone.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A pharmaceutical composition comprising an effective dopaminergic control modulation amount of phosphatidylserine and phosphatidylethanolamine, together with a pharmaceutically acceptable carrier, diluent or excipient wherein said phosphatidylserine is present in an amount of from 60 to 75 weight percent, and said phosphatidylethanolamine is present in an amount of from 40 to 25 weight percent, said composition being substantially free of secondary hematic coagulation effects said composition being prepared by the process comprising:
    extracting phosphatidylserine from animal brain tissue;
    extracting phosphatidylethanolamine from animal brain tissue; and
    combining about 60 to 75 weight percent of said phosphatidylserine with about 40 to 25 weight percent of said phosphatidylethanolamine extract in an appropriate solvent.

2. A pharmaceutical composition as in claim 1, wherein said phosphatidylserine is present in an amount of about 75 weight percent and said phosphatidylethanolamine is present in an amount of about 25 weight percent.

3. A pharmaceutical composition as in claim 1, wherein said phosphatidylserine is present in an amount of about 65 weight percent and said phosphatidylethanolamine is present in an amount of about 35 weight percent.

4. A pharmaceutical composition as in claim 1, wherein said phosphatidylserine is present in an amount of about 60 weight percent and said phosphatidylethanolamine is present in an amount of about 40 weight percent.

5. A method for the treatment of disorders of the central nervous system by dopaminergic control modulation, comprising administering to a human host an effective dopaminergic control modulating amount of a pharmaceutical composition in accordance with claim 1.

6. A method for the treatment of disorders of the central nervous system by dopaminergic control modulation, comprising administering to a human host an effective dopaminergic control modulating amount of a pharmaceutical composition in accordance with claim 2.

7. A method for the treatment of disorders of the central nervous system by dopaminergic control modulation, comprising administering to a human host an effective dopaminergic control modulating amount of a pharmaceutical composition in accordance with claim 3.

8. A method for the treatment of disorders of the central nervous system by dopaminergic control modulation, comprising administering to a human host an effective dopaminergic control modulating amount of a pharmaceutical composition in accordance with claim 4.

9. A method for the treatment of involution of the senile psycho-motor syndromes, vascular cerebropathy, chronic and prevalent psychic component in old age, senile dementia and pre-senile syndromes subjective to post-trauma, post-anoxic cerebropathy, and extrapyramidal syndromes, comprising administering to a human host an effective amount of a pharmaceutical composition in accordance with claim 1.

10. A method for the treatment of involution of the senile psycho-motor syndromes, vascular cerebropathy, chronic and prevalent psychic component in old age, senile dementia and pre-senile syndromes subjective to post-trauma, post-anoxic cerebropathy, and extrapyramidal syndromes, comprising administering to a human host an effective amount of a pharmaceutical composition in accordance with claim 2.

11. A method for the treatment of involution of the senile psycho-motor syndromes, vascular cerebropathy, chronic and prevalent psychic component in old age, senile dementia and pre-senile syndromes subjective to post-trauma, post-anoxic cerebropathy, and extrapyramidal syndromes, comprising administering to a human host an effective amount of a pharmaceutical composition in accordance with claim 3.

12. A method for the treatment of involution of the senile psycho-motor syndromes, vascular cerebropathy, chronic and prevalent psychic component in old age, senile dementia and pre-senile syndromes subjective to post-trauma, post-anoxic cerebropathy, and extrapyramidal syndromes, comprising administering to a human host an effective amount of a pharmaceutical composition in accordance with claim 4.

13. A method for preparing a phospholipid composition comprising:
   extracting phosphatidylserine from animal brain tissue;
   extracting phosphatidylethanolamine from animal brain tissue;
   combining about 60 to 75 weight percent of said phosphatidylserine extract with about 40 to 25 weight percent of said phosphatidylethanolamine extract in an appropriate solvent;
   agitating the resultant solution;
   filtering the agitated solution; and
   precipitating the filtered solution to thereby obtain a phospholipid composition comprising phosphatidylserine and phosphatidylethanolamine.

14. A method as in claim 13, wherein said appropriate solvent is a 2:1 mixture of methanol:chloroform.

15. A method as in claim 13, wherein said precipitation is conducted in acetone.

16. A method as in claim 13, wherein about 3 parts of phosphatidylserine are combined with about 1 part of phosphatidylethanolamine to thereby obtain a phospholipid composition comprising about 75 weight percent phosphatidylserine and about 25 weight percent phosphatidylethanolamine.

17. A method as in claim 13, wherein about 65 weight percent of phosphatidylserine is combined with about 33 weight percent of phosphatidylethanolamine to thereby obtain a phospholipid composition comprising about 65 weight percent phosphatidylserine and about 35 weight percent phosphatidylethanolamine.

18. A method as in claim 13, wherein about 60 weight percent of phosphatidylserine is combined with about 40 percent of phosphatidylethanolamine to thereby obtain a phospholipid composition comprising about 60 weight percent phosphatidylserine and about 40 weight percent phosphatidylethanolamine.

19. A method for preparing a phospholipid composition comprising:
   extracting phosphatidylserine from animal brain tissue;
   extracting phosphatidylethanolamine from animal brain tissue;
   combining about 3 parts of the phosphatidylserine extract with about 1 part of the phosphatidylethanolamine extract in a mixture of methanol:chloroform (2:1);
   agitating the resultant solution;
   filtering the agitated solution; and
   precipitating the filtered solution in acetone to thereby obtain a phospholipid composition comprising about 75 weight percent phosphatidylserine and about 25 weight percent phosphatidylethanolamine.

20. A method for preparing a phospholipid composition comprising:
   extracting phosphatidylserine from animal brain tissue;
   extracting phosphatidylethanolamine from animal brain tissue;
   combining about 65 weight percent of the phosphatidylserine extract with about 35 weight percent of the phosphatidylethanolamine extract in a mixture of methanol:chloroform (2:1);
   agitating the resultant solution;
   filtering the agitated solution; and
   precipitating the filtered solution in acetone to thereby obtain a phospholipid composition comprising about 65 weight percent phosphatidylserine and about 55 weight percent phosphatidylethanolamine.

21. A method for preparing a phospholipid composition comprising:

extracting phosphatidylserine from animal brain tissue;

extracting phosphatidylethanolamine from animal brain tissue;

combining about 3 parts of the phosphatidylserine extract with about 2 parts of the phosphatidylethanolamine extract in an appropriate solvent;

agitating the resultant solution;

filtering the agitated solution; and precipitating the filtered solution to thereby obtain a phospholipid composition comprising about 60 weight percent phosphatidylserine and about 40 weight percent phosphatidylethanolamine.

* * * * *